(12) United States Patent
Niazi

(10) Patent No.: US 8,413,817 B2
(45) Date of Patent: Apr. 9, 2013

(54) NON-BLOCKING FILTRATION SYSTEM

(75) Inventor: Sarfaraz Khan Niazi, Deerfield, IL (US)

(73) Assignee: Therapeutic Proteins International, LLC, Chicago, IL (US)

( * ) Notice: Subject to any disclaimer, the term of this patent is extended or adjusted under 35 U.S.C. 154(b) by 0 days.

(21) Appl. No.: 13/402,948

(22) Filed: Feb. 23, 2012

(65) Prior Publication Data

US 2012/0152862 A1     Jun. 21, 2012

Related U.S. Application Data

(63) Continuation of application No. 13/149,856, filed on May 31, 2011.

(51) Int. Cl.
*B01D 29/90* (2006.01)
*B01D 29/92* (2006.01)
*B01D 35/22* (2006.01)

(52) U.S. Cl.
USPC ........... 210/413; 210/107; 210/219; 210/252; 210/258; 210/321.6; 210/391; 210/406; 210/407; 210/416.1; 210/433.1

(58) Field of Classification Search .................. 210/107, 210/109, 134, 143, 205, 209, 213, 219, 252, 210/257.1, 258, 295, 319, 321.6, 321.65, 210/321.69, 321.75, 31.84, 391, 406, 407, 210/408, 413, 416.1, 433.1, 459, 497.01, 210/498
See application file for complete search history.

(56) References Cited

U.S. PATENT DOCUMENTS

| | | | | |
|---|---|---|---|---|
| 3,075,914 | A * | 1/1963 | Goodmann et al. | 208/199 |
| 3,421,745 | A * | 1/1969 | Prupis | 261/35 |
| 5,443,985 | A | 8/1995 | Lu et al. | |
| 5,457,251 | A * | 10/1995 | Yamashita et al. | 585/269 |
| 6,544,788 | B2 | 4/2003 | Singh | |
| 8,123,948 | B2 * | 2/2012 | Jensen | 210/652 |

* cited by examiner

*Primary Examiner* — John Kim
(74) *Attorney, Agent, or Firm* — Sarfaraz K. Niazi

(57) ABSTRACT

A non-blocking filtration system wherein the suspension filtered continuously scrubs the filter, keeping it free of deposits of solid deposits while the filtrate is removed in a variety of biological and chemical applications, substantially reducing the cost of unit operations.

18 Claims, 1 Drawing Sheet

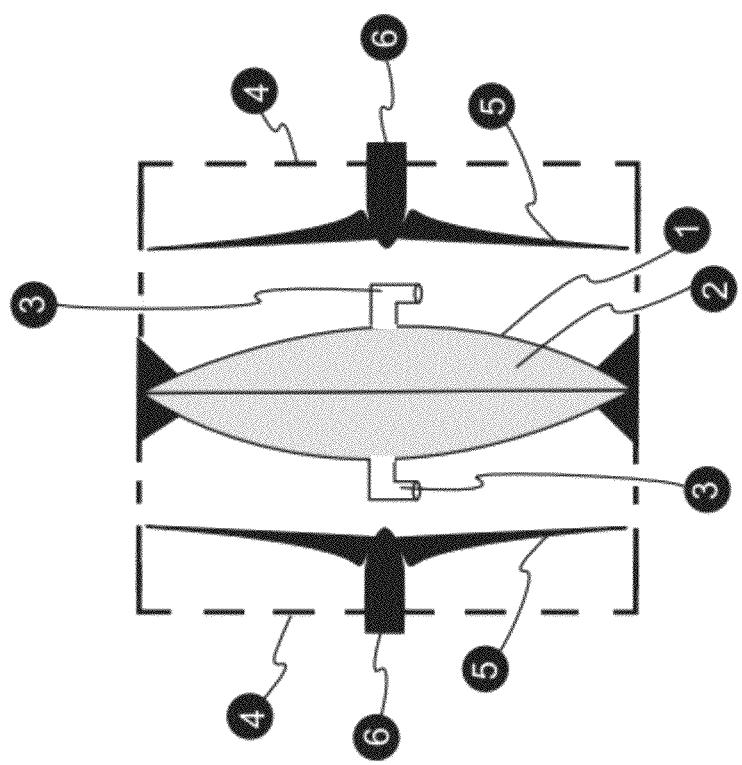

NON-BLOCKING FILTRATION SYSTEM

This application is a continuation of U.S. patent application Ser. No. 13/149,856 filed May 31,2011.

TECHNICAL FIELD OF THE INVENTION

The present invention relates to the field of filtering, more precisely to a method and an apparatus for the separation of suspended matter from filtrate and the use of said method and apparatus wherein either the filtrate or the filtrate is the target product.

BACKGROUND OF THE INVENTION

Separation of suspended matter from liquid is known in the art. Methods such as precipitation, centrifugation and filtering are commonly used for separation purposes in a vast number of industries including chemical and bioprocess industry. The latter separation method is relevant for the present invention.

Several problems concerning the separation of suspended matter from liquid exist, most significantly the blocking of the filter material used that requires replacement of filters, prolong filtration cycles, use of additional containers and eventually high cost. In those instances where the suspended material is a biological entity, the current methods include either centrifugation of the suspended entities or the use of cross-flow filtration methods to reduce the volume, both of which are cumbersome, require large vessels for receiving the filtrate and frequently strain the material contained in the solution causing significant decrease in the productivity of the process.

Centrifugation is a very expensive separation method. When filtering liquids having a high suspended matter content there are significant problems concerning accumulation of suspended matter on the filter. This accumulation is known as the filter cake. In conventional methods the filter cake will grow until further filtering is impossible and the filter then has to be cleaned. There are various techniques for limiting the filter cake. One such technique is cross-flow. Here, the filter is kept clean by continuously scrubbing it with high-speed gas bubbles.

Another filtering method is back flushing. Here, the movement of the suspension is reversed to lift the filter cake from the filter. When using the cross-flow or back flushing methods the filter cake is not accumulated on the filter but is accumulated in the suspension. This requires the filtering process to be either stopped or for the existence of an outlet for the accumulated suspended matter. In the latter situation the removed suspended matter will still have a relatively high liquid content.

A further filtering method is flushing. The filtering process is stopped and the filter is washed. Here, the suspended matter is accompanied by a lot of liquid.

Another field of filtration that has dire need for improvement includes biological manufacturing of drugs, more particularly recombinant drugs where large scale separation of biological culture, reduction in the volume of nutrient media is required both as the end process or during the manufacturing process. There is not suitable device available to provide this functionality at an affordable cost reported in the prior art.

The above problems are overcome by the present invention by presenting a method and an apparatus capable of continuously removing suspended matter from a liquid, and thereby provide a method and apparatus capable of operating continuously without getting blocked and at the same time having an increased filtering capacity and a economical advantage over the prior art.

SUMMARY OF THE INVENTION

The present invention concerns a method for separating suspended matter from liquid, comprising the steps of providing a filter assembly comprising a solid filter with a hollow inner volume; providing a means of scrubbing the filter by high-speed liquid that is subject to filtration, to remove any particles that adhere to the filter; drawing the filtrate inside the hollow filter and continuing the process until the desire volume of liquid is removed from the suspension.

BRIEF DESCRIPTION OF DRAWING

FIG. 1 is the side view of a filter assembly showing the disc filter and turbine propellers disposed on both sides of the disk filter.

DETAILS OF THE INVENTION

Filtration is the process of separating suspended solid matter from a liquid, by causing the latter to pass through the pores of some substance, called a filter. The liquid that has passed through the filter is called the filtrate. The filter may be paper, cloth, cotton-wool, asbestos, slag- or glass-wool, unglazed earthenware, sand, or other porous material.

Filtration is very frequently employed in chemical technology, and it often presents great difficulties. In most technical operations, cotton cloth is the filtering material, but occasionally woolen or haircloth is necessary. The cloth may be fastened on a wooden frame in such a way that a shallow bag is formed, into which the turbid liquid is poured. The filtrate, in this ease, is cloudy at first, but soon becomes clear, and then the turbid portion is returned to the filter. Filtration is often retarded by the presence of fine, slimy precipitates, or by the formation of crystals in the interstices of the cloth, from the hot solution. Any attempt to hasten filtration, by scraping or stirring the precipitate on the cloth, will always cause the filtrate to run turbid.

A better form is the "bag-filter," which is a long, narrow hag of twilled cotton, supported by an outside cover of coarse, strong netting, capable of sustaining a considerable weight and hydrostatic pressure. These bags are often five or six feet long, and eight inches or more in diameter. The open end of the bag is tied tightly around a metallic ring or a nipple, by which the whole is suspended, and through which the liquor to be filtered is introduced. When hot liquids are filtered, the bags are often hung in steam-heated rooms, the temperature being nearly that of the liquid.

In pressure filtration, the liquid is forced through the interstices of the filter by direct atmospheric pressure, the air being exhausted from the receiver; or by hydrostatic pressure, obtained either by means of a high column of the liquid, or by a force pump. By the first method, called suction filtration, the liquid may be forced downward through the filter into a receiver; the precipitate collects on the top of the filter and becomes a part of the filtering layer. This sometimes causes difficulty, for the particles of certain precipitates unite to form an impervious layer. Or the filtrate may be drawn upwards through the filter, which is suspended in the liquid to be filtered; thus clogging does not occur so easily, as a large part of the precipitate settles to the bottom of the vessel and does not come in contact with the filter until most of the liquid has been drawn off.

In technical work, the filter press usually obtains pressure. This is a strong iron frame, in which a number of cast-iron or bronze filter cells are supported. Each cell is made up of two flat metal plates with raised edges, separated by a hollow "distance frame" of the same metal. There is a hole in the center of each plate, and grooves on each surface leading to an opening at the lower edge of the plate. A filter is made of two pieces of cloth, slightly larger than the plates, sewed together along the margin of a small circular opening cut in the center of each. One piece of the cloth is passed through the hole in the plate, and then both pieces are spread out smoothly, one on either side of the plate.

Another plate is prepared in the same way, and a distance frame having been placed between them, the cell thus formed is set vertically in the press frame, where it is supported by lugs on each plate and distance frame. When the desired numbers of cells are ready, they are tightly clamped together by means of a heavy screw, which passes through one end of the press frame. Thus a series of cells, lined with filter cloth and connected by a straight channel through the central holes, is formed. A powerful force pump drives the liquid to be filtered into the cells, where it passes from one to the other until they are all filled. The hydrostatic pressure forces the liquid through the filters into the grooves in the plates, along which it flows, and escapes through the openings at the lower side of the plate. The sediment retained by the cloth collects ill the cell and forms a solid cake, which finally fills each cell completely. The process is then stopped, the cells taken apart, and the cake of sediment having been removed, the cells are returned to the press frame, to be again put into operation. The filtrate is caught in a trough.

In another form of press, instead of the central opening, there is a hole in the cornel of each plate and distance frame in such a position that, when placed in the press, the holes form a continuous channel through the corner of the whole series of cells. A small hole drilled on the inside of each distance frame, at right angles to the direction of the channel, admits the liquid into each cell. The filter is a piece of cloth hung over the distance frame in such a way that both sides of the frame are covered. A frame so covered is put between each pair of grooved plates. Small holes are cut in the cloth to correspond to the channel in the corners of the cells. The method of filtration is the same as in the central feed machines.

The pressure obtained by the force pump may be only a few pounds, or it may rise to several hundred pounds per square inch. The filter press may contain from a dozen to fifty or more cells, and these cells may be as large as four feet in diameter. For many purposes the press is surrounded by coils or jackets, through which steam or refrigerating solutions may be circulated, according as hot or cold filtration is desired. The filter press is very rapid in its action and is extensively employed in industrial chemical work. For use with acid or corrosive liquids, the plates and distance frames are often covered with lead or some alloy, which is not easily corroded.

The centrifugal machine is, to a great extent, replacing the filter press and other filters, especially when crystals are to be removed. This furnishes the most rapid method and leaves the substance almost dry. The centrifugal machine is a cylindrical box or basket of wire gauze or perforated sheet metal, fixed to a vertical shaft, which rotates at a very high speed. The contents of the box are driven to the outer wall by the centrifugal force, the solid matter being retained by the gauze or screen. The liquid passes through and is caught in a fixed shell, surrounding the rotating basket. These machines are of various sizes from 12 to 60 inches diameter, and 8 to 36 inches, depth of basket. Two general forms are in use: the over-driven type, in which the driving pulley is fixed at the upper end of the shaft, above the basket; and the under-driven type, in which the basket is placed on the upper end of the shaft, and the pulley below. In the over-driven type it is frequently customary to suspend the shaft in flexible bearings. Thus the basket is enabled to adjust itself to any change in the center of gravity, caused by unequal loading, and runs without vibration.

Sand filters are sometimes used for work on a large scale. These are made as follows: into a box having a perforated bottom, is put a layer of coarse gravel; this is covered with finer pebbles; these by sand, and a jute or canvas cloth covers the whole. A wooden or iron grating is added to protect the filter, when the sediment is shoveled out. The filter is often placed over a receptacle from which the air may be exhausted, thus affording pressure filtration if necessary.

Bioprocessing requires intensive use of filtration, from sterilizing liquids to separating cells and organisms and to reduce the volume of liquid prior to subjecting it to purification steps.

One of the most common techniques used in the art of bioreaction is to separate the bacteria or cells after the bioreaction cycle completes. In most instances, this would require using very high-speed centrifuges to separate the very fine cells. A centrifuge uses centrifugal force (g-force) to isolate suspended particles from their surrounding medium on either a batch or a continuous-flow basis. Applications for centrifugation are many and may include sedimentation of cells and viruses, separation of subcellular organelles, and isolation of macromolecules such as DNA, RNA, proteins, or lipids.

Many particles or cells in a liquid suspension, given time, will eventually settle at the bottom of a container due to gravity (1×g). However, the length of time required for such separations is impractical. Other particles, extremely small in size, will not separate at all in solution, unless subjected to high centrifugal force. When a suspension is rotated at a certain speed or revolutions per minute (RPM), centrifugal force causes the particles to move radially away from the axis of rotation. The force on the particles (compared to gravity) is called Relative Centrifugal Force (RCF). For example, an RCF of 500×g indicates that the centrifugal force applied is 500 times greater than earth's gravitational force.

In differential centrifugation separation is achieved primarily based on the size of the particles in differential centrifugation. This type of separation is commonly used in simple pelleting and in obtaining partially pure preparation of subcellular organelles and macromolecules. For the study of subcellular organelles, tissue or cells are first disrupted to release their internal contents. This crude disrupted cell mixture is referred to as a homogenate. During centrifugation of a cell homogenate, larger particles sediment faster than smaller ones and this provides the basis for obtaining crude organelle fractions by differential centrifugation. A cell homogenate can be centrifuged at a series of progressively higher g-forces and times to generate pellets of partially purified organelles.

When a cell homogenate is centrifuged at 1000×g for 10 minutes, unbroken cells and heavy nuclei pellet to the bottom of the tube. The supernatant can be further centrifuged at 10,000×g for 20 minutes to pellet subcellular organelles of intermediate velocities such as mitochondria, lysosomes, and microbodies. Some of these sedimenting organelles can obtained in partial purity and are typically contaminated with other particles. Density gradient centrifugation is the preferred method to purify sub-cellular organelles and macromolecules. Placing layer can generate density gradients after layer of gradient media such as sucrose in a tube with the heaviest layer at the bottom and the lightest at the top in either a discontinuous or continuous mode. The cell fraction to be separated is placed on top of the layer and centrifuged. By using the method and/or apparatus of the invention a substantially suspended filter cake is obtained. In a further aspect of the invention the use of such substantially suspended filter cake is within the scope of the invention.

The present invention further focuses on the use of the above method and apparatus.

While centrifugation plays a vital role in biological research and manufacturing, the problem starts when very large volumes of very dilute solutions are centrifuged; since a centrifuge must run for a specific time at a very high gravity, the design of centrifuges is complex and their cost very high. Continuous flow centrifuges capable of processing of hundreds and thousands of liters of suspension cost into hundreds of thousands dollars and require very high maintenance. There is an unmet need in the art to design a method of reducing the volume of suspension substantially so that smaller size centrifuges, which cost substantially less, can be used to perform a unit operation. Fermentation tanks used for recombinant manufacturing of drugs often contain thousands of liters of media and recently processing tanks as large as 100,000 liters have been installed. The current art does not provide any solution to handle such large volumes of suspensions except, either centrifuge the entire volume or subject it to a cross-flow separation prior to centrifugation. Both of these approaches are extremely cumbersome, expensive to install and operate. The instant invention provides an ideal solution for this unmet need. Since filtration of large volumes of suspensions inevitably results in the blockage of filters and additional cost filtration apparatus that is operated under high pressure, these techniques, while useful, offer the most expensive solutions.

A major application of the claimed device is in the field of perfusion operations in a bioreactor or in vessels used to hold artificial organs and in cell therapy. Cell culture has generated considerable interest in recent years due to the revolution in genetic engineering and biotechnology. Cells are cultured to make proteins, receptors, vaccines, and antibodies for therapy, research, and for diagnostics.

Traditionally, cell culture has been operated in a batch mode. In batch operation, the bioreactor is seeded with a small amount of cells and the cells are grown to high density. The cells secrete the product of interest and eventually die due to lack of nutrients at which point the culture is harvested. This method has several drawbacks: firstly, a large fraction of nutrients are wasted in simply growing up cells and are not used directly for making the product; secondly, product formation is often inhibited due to the buildup of toxic metabolic byproducts; and lastly critical nutrients are often depleted leading to low cell densities and consequently lower product yields.

It has long been recognized that perfusion culture offers better economics. In this operation, cells are retained in the bioreactor, and the product is continuously removed along with toxic metabolic byproducts. Feed, containing nutrients is continually added. This operation is capable of achieving high cell densities and more importantly, the cells can be maintained in a highly productive state for weeks and even months. This achieves much higher yields and reduces the size of the bioreactor necessary. It is also a useful technique for cultivating primary or other slow growing cells.

The idea of perfusion has been known since the beginning of the century, and has been applied to keep small pieces of tissue viable for extended microscopic observation. The technique was initiated to mimic the cells milieu in vivo where cells are continuously supplied with blood, lymph, or other body fluids. Without perfusion, cells in culture go through alternating phases of being fed and starved, thus limiting full expression of their growth and metabolic potential. The current use of perfused culture is in response to the challenge of growing cells at high densities (i.e., $0.1$-$5 \times 10^8$ cells/ml). In order to increase densities beyond $2$-$4 \times 10^6$ cells/ml, the medium has to be constantly replaced with a fresh supply in order to make up for nutritional deficiencies and to remove toxic products. Perfusion allows for a far better control of the culture environment (pH, $pO_2$, nutrient levels, etc.) and is a means of significantly increasing the utilization of the surface area within a culture for cell attachment.

Perfusion cell culture has long been used as a method of achieving higher cell densities and increased culture length when compared to batch culture methods. The greater cell density and longer culture life can result in better yields of secreted products, more efficient use of media and the ability to generate large numbers of cells in small volumes. The greatest challenge of perfusion cell culture has always been the need to contain the cells within the culture without reducing cell viability. Filters have traditionally been used to contain the cells, and elaborate methods have been devised to prevent the filters from fouling and shortening the length of the perfusion culture. All of these steps add substantial cost to the manufacturing process.

The U.S. Pat. No. 5,443,985 suggests that to prevent the clogging of the perfusion filter, it should be placed in the upper part of an inclined bioreactor where it is less likely to encounter the cells that might block the filter.

The U.S. Pat. No. 6,544,788 to Singh discloses a perfusion filter with neutral buoyancy that allows this 'lily pad' filter to float just under the surface of the media where the wave action that mixes and oxygenates the culture helps wash the filter. The gentle washing prevents the filter from clogging and extends the length of the perfusion culture while maintaining a low shear environment for the cells. This invention is of little use in bioreactors where the suspension culture is maintained rather homogenous throughout the bioreactor obviating any advantage of keep the filter floating at the surface where the cell count is expected to be the lowest; this may be of some value in rocking platform bioreactors like the GE Wave Bioreactor but for large scale suspension culture where the cells are kept in uniform suspension, both of the above prior art disclosures are of little practical value.

The development of a perfused packed-bed reactor using a bed matrix of a non-woven fabric has provided a means for maintaining a perfusion culture at densities exceeding $10 \times 10^8$ cells/ml of the bed volume (CelliGen, New Brunswick Scientific, Edison, N.J.). However, like other such methods, these devices have high cost and limited applications.

Perfusion operations have tremendous potential for growing the large number of cells needed for human cell and genetic therapy applications.

The central problem in perfusion culture is how to retain the cells in the bioreactor. Prior art can be classified into four basic separation technologies: filtration, gravity sedimentation, centrifugation and continuous perfusion. Filtration methods require some means to keep the filter from clogging over the required weeks of operation. Cross-flow filters are typically used. Here a high tangential liquid velocity is used to keep the surface clean. Spinning filters are another embodiment of this concept. Gravity sedimentation can be used to separate the cells and several types of inclined settlers have been reported. The major problem with settlers is the varying sedimentation characteristics of different cells and the difficulty in scale-up to industrial systems. Centrifugation has found limited application in cell culture due to the difficulty in maintaining sterility. The first three methods share a common weakness--in that the liquid from the bioreactor must be pumped through the separation device and the cell-enriched material returned to the bioreactor. Keeping this recirculation loop sterile is difficult, and contamination often occurs. To maintain the high cross-flow velocity necessary to prevent clogging, the cells are subjected to high pumping shear in the recirculation loop and are often damaged. Oxygen depletion can also occur if the pumping rate is too slow. These factors often lead to degradation in product quality and quantity. The fourth type of method avoids some of these problems by eliminating the need to use a pump-around loop wherein nutrient media is removed from the bioreactor and replaced with fresh media by filtering the contents of the bioreactor continuously.

However, the method of removing nutrient media from a bioreactor and replacing it with fresh media becomes a difficult process when using thousand of liters of nutrient media and very high density of cell culture, as it is becoming a normal exercise in commercial production. Whether it is placing the filter in a special place in the bioreactor to reduce exposure to high cell titer or gently shaking the filter to keep the filter from getting clogged, these prior art methods are inadequate for large-scale commercial production. Even if the perfusion is performed at a rate of one to two media volume exchanged per day, bioreactors containing thousands of liters with suspension culture at high titer would make it impossible to use any of the current art to accomplish the filtration and harvesting of the nutrient media. Large-scale filtration would require faster passage of media through the filter and that would inevitably bring cell culture in direct contact with filter surface resulting in fouling and blockage of the filters. Unfortunately, the flexible and disposable bioreactors wherein most of the art of perfusion filtration is developed are not suitable for large-scale operations and thus the dearth of technology in the field of cell culture processing was not fully appreciated.

There is therefore a dire need to invent systems useful for any size of operation, ones that could not be blocked regardless of the rate of filtration and ones that could be sterilized and be also affordable. The instant invention resolves all of these problems by utilizing a method scrubbing the filter surface by using the medium filtered itself as a source of scrubbing a filter membrane responsible for removing the nutrient media while leaving the cells inside the bioreactor.

The present invention provides an inexpensive perfusion filtration system that does not require any external loop or recirculation pump. Thus, it is much simpler, has lower cost, and is less prone to contamination than conventional devices. The perfusion bioreactor may be used to produce secreted products, produce large amounts of slow growing cells, or function as an artificial organ such as an extracorporeal liver. The simple construction and sterile design of the filter assembly make it ideal for hospital use in cell and gene therapy applications. The process of water purification was described in writings in ancient Greek and Sanskrit as early as 2000 BCE. Methods utilized by these peoples included sand and gravel filtration, straining and boiling. While the science of filtration may not have been evident to early inventors, today, the science of filtration has yielded some of the most significant invention in the art of separation if components, not just dissolved and un-dissolved but even types of dissolved components. The most common type of filtration would be to force the solution through a membrane of finite pore size that would retain the smallest size of the component to be separated. Often, it is filtrate that is desired but mostly it is the filtered material.

Microfiltration refers to removing very fine particles including bacteria and cells; a typical sterilizing filter would have a pore size of about 0.22 microns, however, in many biological processes, such small pore size is not necessary since the purpose is to remove a certain mass of cells, whose size is well known. For example, the Chinese Hamster Ovary cells, the most common engine for recombinant expression of proteins takes a filter of about 5 microns in diameter to filter out. It is important to realize that the smaller the pore size, the greater is the pressure required to force the flow of liquid and greater is the chance of blocking the pores. As a result, microfiltration has been replaced by other means such as centrifugation to remove cells in many industrial processes. However, if a system can be developed wherein large quantities of suspended cells can be removed without blocking the filters, this would always be preferred as it obviates the need for another unit process.

The instant invention offers a novel solution in the art of filtration wherein the filters are kept from getting blocked through continuous scrubbing by fine gas bubbles. Introduction of gas bubbles will have additional benefits in improving aeration and the process of aeration can be utilized for a dual purpose in some situations, to grow cells and to filter out cells in the same container and at the same time with remarkable cost and timesaving.

For the purposes of illustrating the invention, there is shown in the drawings a form which is presently preferred, it being understood however, that the invention is not limited to the precise form shown by the drawing in which:

The pore size of the perfusion filter is important and dependent on the specific process for which it is used; generally, the average diameter of CHO cells is 14-15 microns but here is a distribution of sizes with a sharp fall in the distribution below 8 microns; so while, a 7 micron filter (as used in U.S. Pat. No. 6,544,788) will be useful, it leaves the possibility of losing a substantial number of cells smaller than 7 microns in size. The instant invention set a limit of 5 micros for the perfusion filter as the cut off for more 99% CHO cells while maintaining the fast flow through the filter. Other methods such as U.S. Pat. No. 65,544,788 cannot afford to use a smaller size filter because of the blockage that can easily occur with smaller pore sizes as they produce a greater filtration pressure.

In a first embodiment, the instant invention discloses a filtration assembly comprising a filter capable of separating suspended cells from the media, a turbine propeller and an arrangement of the two in such configuration that the liquid propelled on to the surface of the filter continuously flushes the outer surface of the filter. This allows continuous scrubbing of the external surface of the filter and keeping the surface clean at all time for long-term perfusion.

In a second embodiment, the instant invention discloses a design of a filter assembly comprising a disc shaped hollow filter with a hard surface and a pore size ranging between 1 to 100 microns to allow filtration of all types of chemical and biological suspensions except those that require sterilization from bacterial contamination.

In a third embodiment, the instant invention discloses a method of using the instant invention to sterilize liquids by providing filtration membrane capable of filtering out objects of down to 0.1 microns; the hard surface of the filter provides a stable base for the installation of these filter sheaths which are very delicate.

In a fourth embodiment, the instant invention discloses the use of ceramic material structures such as tube, disc, ovoid or rectangle to serve as perfusion filter with pore sizes of 50 micron or less.

In a fifth embodiment, the instant invention discloses myriad of possibilities of using it in chemical and biological industrial applications.

In a sixth embodiment, the instant invention discloses a method of perfusion to recover biological products from a bioreactor and to allow long-term operation of bioreactors by retaining the cell culture within the bioreactor and extends the use to preservation of organs.

In an seventh embodiment, the instant invention provides means of adjusting the intensity of liquid scrubbing system by monitoring the amount of vacuum needed to draw a predetermined volume of liquid and thus assuring that the perfusion filter is kept clean, The components of the filtration devices described herein which come into contact with the culture medium or products provided thereby desirably comprise biocompatible materials, more desirably biocompatible polymers, and are preferably sterilizable.

In the instant invention, a filtration system that comprises a hard porous surface that has pores in the size range of 0.1 to 1 mm. Ideally, this would be a hollow disc, which is attached to a high vacuum on both sides to such means as a peristaltic pump or even ordinary pumps where the drawn liquid is discarded or collected depending on whether the object is to modify a suspension or to collect a mother-liquor. The disc is optionally covered with a membrane filter with pores ranging down to 0.1 microns to 100 microns. The hard surface of the disc serves as a support surface to allow use of any type of filter without letting it collapse under vacuum. However, any withdrawal of liquid would inevitably cause the surface of the filter membrane to get blocked quickly and that is prevented in the instant invention by continuously scrubbing of the surface of the filter with high-speed flow of the suspension being cleared.

In the operation of the instant invention, the suspension is forced to strike the surface of the membrane filter by means of a turbine propeller of about the same diameter as the diameter of the disc and disposed within 0.1 cm to 1 cm away from the filter surface on each side. The suspension is drawn from one side of the turbine propeller and blasted over the filter on the other side. As the suspension is driven at a high speed, the suspended particles and the moving liquid acquire higher momentum and are able to knock off any suspended particles sticking to the filter. The turbine propeller and the disc are placed inside a housing to assure that they remain correctly juxtaposed. The power to drive the turbine propeller can come from an electric motor either installed outside of the filter assembly and a rotating cable driving the turbine propeller or the motor can be installed on the propeller directly or a source of compressed gas can be used to drive the turbine propeller. The rotational speed of the turbine propeller is adjusted automatically depending on the force needed to draw the filtrate out of the suspension; the more the membrane filter is blocked, the more is the force of vacuum required to draw the filtrate out and thus a higher speed of rotation of the turbine propeller would be needed to keep the surface clean. The turbine propeller would generally be operated between 100 to 1000 rpm.

By adjusting the speed of scrubbing, the filter surface can be kept clean and unblocked indefinitely allowing continuous movement of liquid but leaving the suspended particles in the container. The instant invention would therefore work whether the intent is to collect the suspended particles like bacterial and CHO cells or the filtrate containing a solution of a drug.

Similar applications are envisioned in the chemical industry, water purification industry and any such application where very fine to very crude suspended particles are to be removed from a suspension.

FIG. 1 shows a preferred embodiment of the filter comprising a housing 4 containing the filter disc 1 with a plurality of pores 2 and liquid outlets 3; the turbine propellers 5 placed in a perforated housing 4, and the turbine propeller 5 is operated by a motor 6 that can be operated remotely to the device.

The disc can be ideally made from a ceramic material such as aluminum oxide, the key features required are that the material be hard to withstand the pressure applied to draw the liquid without collapsing and can be formulated to provide the required porosity. The type of material used for the filter is not important as long as it can be fabricated with the above qualification. The shape of the filter is ideally a disc but it can be a ovoid, cuboid or any shape as long as it meets the requirements of sturdiness and porosity and the requirement that the porous surface is fully exposed to the action of scrubbing suspension.

It is further envisioned that the disc is optionally covered by a nylon filter sheath to provide any desirable pore size as well as to exploit the electrical charge on the nylon sheath that might itself help to repel the suspended cells and particles from sticking to the surface if their charge is the same as the charge on the nylon membrane. As a example, Pall Corporation provides filters (www.pall.com) made of nylon that are amphoteric, positively or negatively charged at neutral pH. The Porex Company (www.porex.com) offers many interesting possibilities; for example, X-7744 T3 is a hydrophobic polyethylene sheet with a pore size of 10 Microns that can be readily wrapped around the filter. The porosity of the membrane filter is important if the intent is to remove biological entities such as bacteria and Chinese Hamster Ovary cells or to sterilize a liquid such as in water purification.

EXAMPLES

Example 1

The device shown in FIG. 1 is inserted in a bioreactor at the end of a bioreaction cycle wherein the goal was to express erythropoietin using Chinese Hamster Ovary cells, liquid flow was started and the culture media withdrawn at a rate of about 5 L/minute; a total volume of 50 L was reduced to 5 liters in less than 10 minutes.

Example 2

The device shown in FIG. 1 was inserted in a bioreactor at the end of a bioreaction cycle where the aim was to grow recombinant *E. Coli* capable of expressing filgrastim, and the total volume of 50 L was reduced to 5 L by removing 45 liters of the media in less than 10 minutes. This was accomplished by first turning on the turbine propeller s and then applying a vacuum by drawing the filtrate using a peristaltic pump. At the end of the cycle, the 5 L media with bacterial cells was centrifuged to form a pellet mass and further processed. This obviated the need to centrifuge 50 L of media.

Example 3

The device shown in FIG. 1 was disposed inside a disposable bioreactor and pre-sterilized using gamma radiation; a recombinant product was produced in the disposable bioreactor by adding sufficient quantity of nutrient media and CHO cells; the nutrient media was removed gradually such that two volumes of the nutrient media is replaced per day; this allowed very high level of productivity for the production of beta interferon.

It should also be understood that many of the components described herein also are desirably flexible, e.g., the disc and the turbine propeller and the housing associated with them desirably comprise flexible biocompatible polymer containers, with the conduits also desirably comprising such biocompatible polymers. The flexible material is further desirably one that is USP Class VI certified, e.g., silicone, polycarbonate, polyethylene, and polypropylene. Non-limiting examples of flexible materials include polymers such as polyethylene (e.g., linear low density polyethylene and ultra low density polyethylene), polypropylene, polyvinylchloride, polyvinyldichloride, polyvinylidene chloride, ethylene vinyl acetate, polycarbonate, polymethacrylate, polyvinyl alcohol, nylon, silicone rubber, other synthetic rubbers and/or plastics. If desired, portions of the flexible container may comprise a substantially rigid material such as a rigid polymer (e.g., high density polyethylene), metal, and/or glass.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A filtration system to remove a filtrate from a suspension comprising:
   a. a circular porous disc with two sides and an inner volume, a plurality of pores ranging from 1 micron to 100 microns and a filtrate port on each side of the disc;
   b. a source of vacuum connected to each filtrate port;
   c. a turbine propeller assembly equal in diameter to the diameter of the disc and positioned at a distance between 0.1 cm to 1 cm away from the each side of the disc, a means of rotating the turbine propeller and a means of controlling the speed of rotation of the turbine propellers;
   d. a housing to hold the disc and the turbine propellers in place.

2. The filtration system according to claim 1, wherein the disc is covered by a filter membrane with a plurality of pores ranging from 0.1 µm to 5 µm.

3. The filtration system according to claim 1, wherein the disc is made of polymer, ceramic or metal.

4. The filtration system according to claim 3, wherein the ceramic material is aluminum oxide.

5. The filtration system according to claim 2, wherein the filter membrane is made of cellulose, polyethylene or nylon.

6. The filtration system according to claim 1, wherein the turbine propellers are capable of drawing a suspension and blowing it at a high velocity in the surface of the disc.

7. The filtration system according to claim 1, wherein the turbine propeller assembly is made of a polymer or metal.

8. The filtration as system according to claim 1, wherein the means of rotating the turbine propeller comprise a rotating cable connected to the propeller through gears, a gas driven motor or an electric motor.

9. The filtration system according to claim 1, wherein the turbine propeller is capable of rotating continuously from 100 rpm to 1000 rpm.

10. The filtration system according to claim 1, wherein the speed of the turbine propeller is automatically adjusted directly in proportion to the intensity of vacuum required for withdrawing the filtrate.

11. The filtration system according to claim 1, wherein the vacuum source is a peristaltic pump.

12. The filtration system according to claim 1, wherein the suspension comprises a nutrient media and a biological culture.

13. The filtration system according to claim 1, wherein the filtration system is disposed completely inside a disposable bioreactor.

14. The filtration system according to claim 1, wherein the filtration system is disposable.

15. The filtration system according to claim 1, wherein it is used as a perfusion filter in the manufacturing of recombinant drugs using cell culture.

16. The filtration system according to claim 1, wherein it is used as a perfusion filter in the clearing of biological fluids of contaminants in clinical use.

17. The filtration system according to claim 1, wherein it is used to sterilize contaminated liquids in various process industries.

18. The filtration system according to claim 1, wherein the filtrate removed is the desired product.

* * * * *